(12) United States Patent
Carr et al.

(10) Patent No.: US 7,981,280 B2
(45) Date of Patent: Jul. 19, 2011

(54) RECIRCULATION OF BLOOD IN AN EXTRACORPOREAL BLOOD TREATMENT SYSTEM

(75) Inventors: David J. Carr, West Lafayette, IN (US); Stephen R. Ash, Lafayette, IN (US)

(73) Assignee: Renal Solutions, Inc., Warrendale, PA (US)

( * ) Notice: Subject to any disclaimer, the term of this patent is extended or adjusted under 35 U.S.C. 154(b) by 1001 days.

(21) Appl. No.: 11/443,699

(22) Filed: May 31, 2006

(65) Prior Publication Data

US 2007/0158247 A1    Jul. 12, 2007

Related U.S. Application Data

(60) Provisional application No. 60/756,782, filed on Jan. 6, 2006.

(51) Int. Cl.
*B01D 61/28* (2006.01)
*B01D 61/32* (2006.01)
*B01D 61/00* (2006.01)

(52) U.S. Cl. ......... 210/134; 210/85; 210/96.2; 210/141; 210/143; 210/194; 210/195.2; 210/252; 604/6.09; 604/6.11; 604/65; 604/66; 604/67

(58) Field of Classification Search ............ 210/85, 210/96.2, 134, 141, 143, 194, 195.2, 252; 604/6.09, 6.11, 65, 66, 67

See application file for complete search history.

(56) References Cited

U.S. PATENT DOCUMENTS

| | | | |
|---|---|---|---|
| 4,185,629 A | 1/1980 | Cullis et al. | |
| 4,223,672 A | 9/1980 | Terman et al. | |
| 5,591,344 A | 1/1997 | Kenley et al. | |
| 5,650,071 A | 7/1997 | Brugger et al. | |
| 5,951,870 A | 9/1999 | Utterberg | |
| 5,964,724 A | 10/1999 | Rivera et al. | |
| 6,083,187 A | 7/2000 | Nakayama et al. | |
| 6,187,198 B1 | 2/2001 | Utterberg | |
| 6,344,139 B1 | 2/2002 | Utterberg | |
| 6,464,878 B2 | 10/2002 | Utterberg | |
| 6,475,178 B1 | 11/2002 | Krajewski et al. | |
| 6,638,477 B1 | 10/2003 | Treu et al. | |
| 7,273,465 B2 | 9/2007 | Ash | |
| 2001/0045395 A1 | 11/2001 | Kitaevich et al. | |

(Continued)

FOREIGN PATENT DOCUMENTS

WO    WO 88/06460    9/1988

*Primary Examiner* — John Kim
(74) *Attorney, Agent, or Firm* — Fish & Richardson P.C.

(57) ABSTRACT

An extracorporeal blood treatment apparatus includes a blood treatment unit, a treatment fluid circuit, and a blood circuit. The treatment fluid circuit has a treatment fluid pump for circulating treatment fluid around the treatment fluid circuit and through the blood treatment unit. The blood circuit has a dual chamber blood pump for circulating blood around the blood circuit and through the blood treatment unit. An arterial line withdraws blood from a patient and delivers the withdrawn blood to the blood treatment unit. A venous line returns the treated blood to the patient. The arterial and venous lines can be switched between a first condition in which they are connected to the patient and a second condition in which they are disconnected from the patient and connected to each other for recirculation of blood through the blood circuit. A controller operates the blood pump, and switches the blood pump between a condition in which the dual chambers operate in phase with each other and a condition in which the dual chambers operate out of phase with each other.

16 Claims, 9 Drawing Sheets

U.S. PATENT DOCUMENTS

2003/0163077 A1 8/2003 Kim et al.
2003/0229302 A1 12/2003 Robinson et al.
2004/0084358 A1 5/2004 O'Mahony et al.
2004/0127840 A1 7/2004 Gara et al.
2005/0274658 A1 12/2005 Rosenbaum et al.

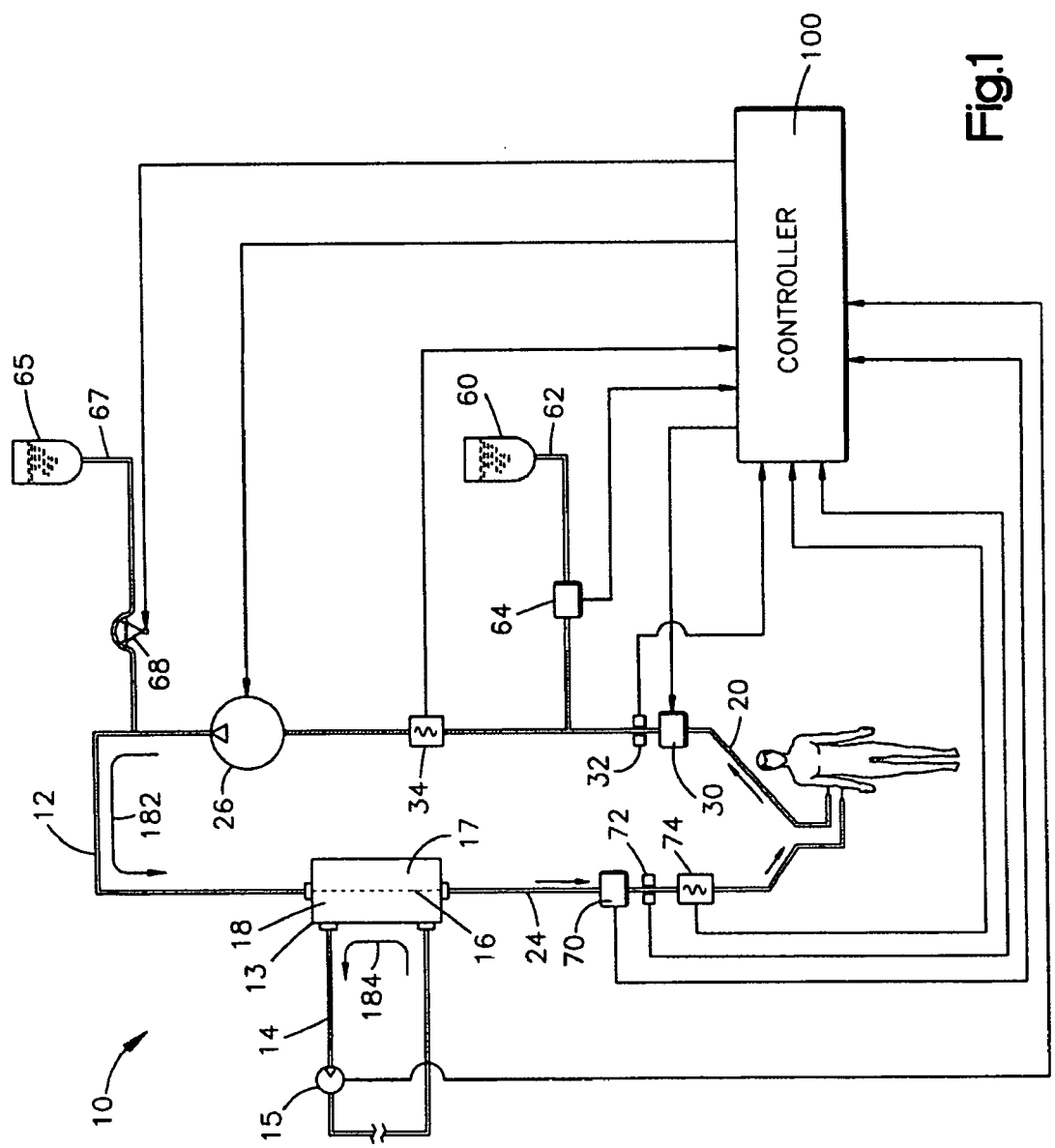

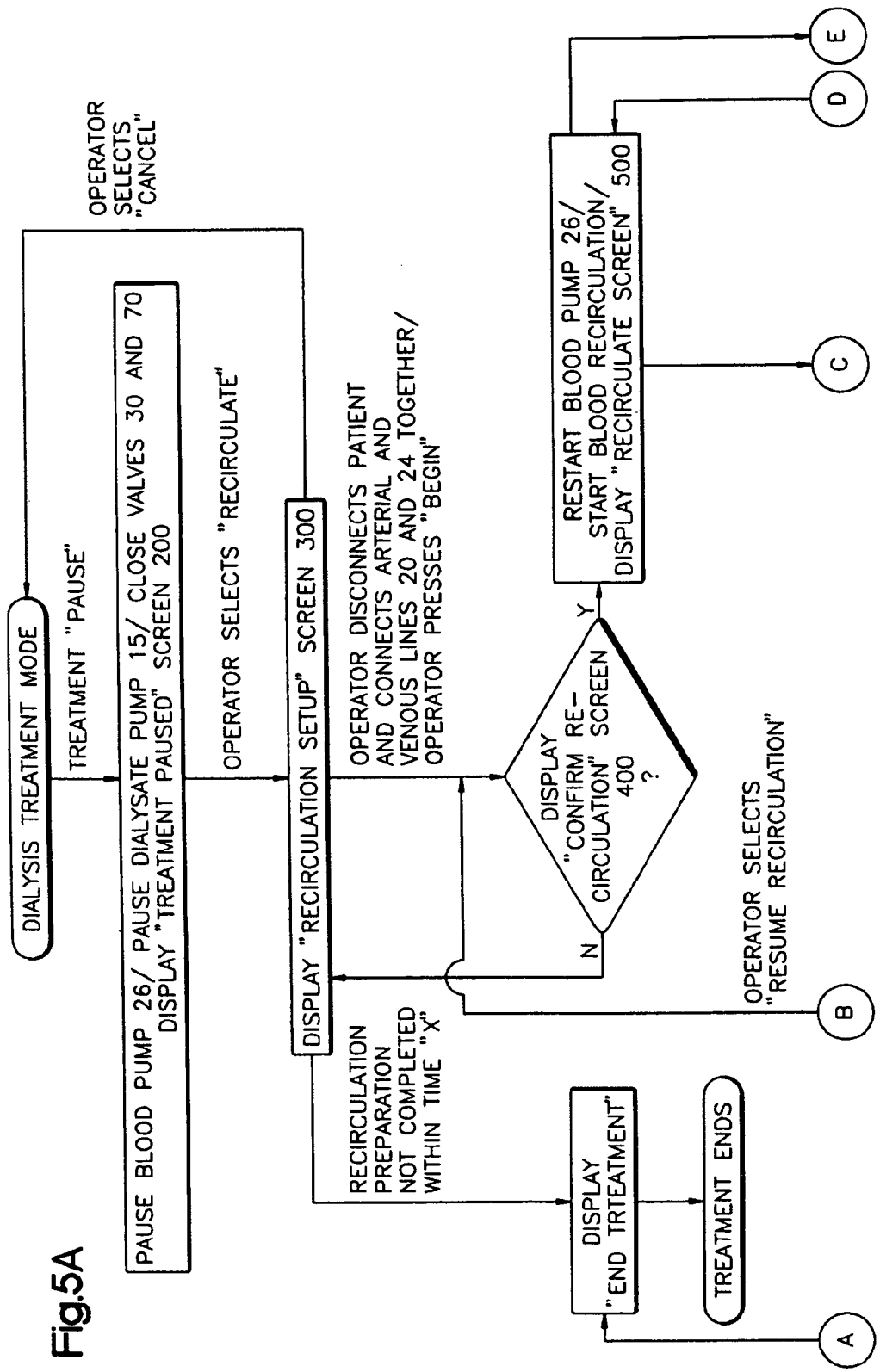

RECIRCULATION OF BLOOD IN AN EXTRACORPOREAL BLOOD TREATMENT SYSTEM

RELATED APPLICATIONS

This application claims the benefit of Provisional Application Ser. No. 60/756,782, filed Jan. 6, 2006, which is incorporated by reference.

FIELD

This invention relates to systems and methods for the extracorporeal treatment of blood.

BACKGROUND

A dialysis system is used as a substitute for the natural kidney function of a human body. The dialysis system cleans the blood of the natural accumulation of bodily wastes by separating the wastes from the blood in an extracorporeal blood treatment apparatus. The separated wastes are discharged and the cleansed blood is returned to the body.

The dialysis system includes a blood tubing set, a dialysate tubing set, a dialysate fluid, and a dialyzer where the processing of blood takes place. Typically, a dialyzer includes a semi-permeable membrane located within a closed housing which effectively separates the housing into a blood compartment and a dialysate compartment. The blood removed from the patient flows through the blood circuit and enters the blood side of the dialyzer. The dialysate solution is passed through the dialysate side of the dialyzer. The waste from the blood passes through the membrane into the dialysate fluid.

SUMMARY

An extracorporeal blood treatment apparatus includes a blood treatment unit, a treatment fluid circuit and a blood circuit. The treatment fluid circuit has a treatment fluid pump for circulating treatment fluid around the treatment fluid circuit and through the blood treatment unit. The blood circuit has a dual chamber blood pump for circulating blood around the blood circuit and through the blood treatment unit. An arterial line withdraws blood from a patient and delivers the withdrawn blood to the blood treatment unit. A venous line returns the treated blood to the patient. The arterial and venous lines can be switched between a first condition in which they are connected to the patient and a second condition in which they are disconnected from the patient and connected to each other for recirculation of blood through the blood circuit.

The apparatus also includes a controller that operates the treatment fluid pump and the blood pump in a plurality of modes, including a treatment mode and a recirculation mode. In the treatment mode, both the blood pump and the treatment fluid pump are operated to circulate blood and treatment fluid through the blood treatment unit while the arterial and venous lines are in the first condition. In the recirculation mode, the treatment fluid pump is inactivated, and the blood pump is operated to circulate the blood through the blood circuit while the arterial and venous lines are in their second condition. The controller is further configured to switch the blood pump between a condition in which the dual chambers operate in phase with each other and a condition in which the dual chambers operate out of phase with each other.

BRIEF DESCRIPTION OF THE DRAWINGS

FIG. 1 is a schematic view of an extracorporeal blood treatment system.

DESCRIPTION

Figure 1A:
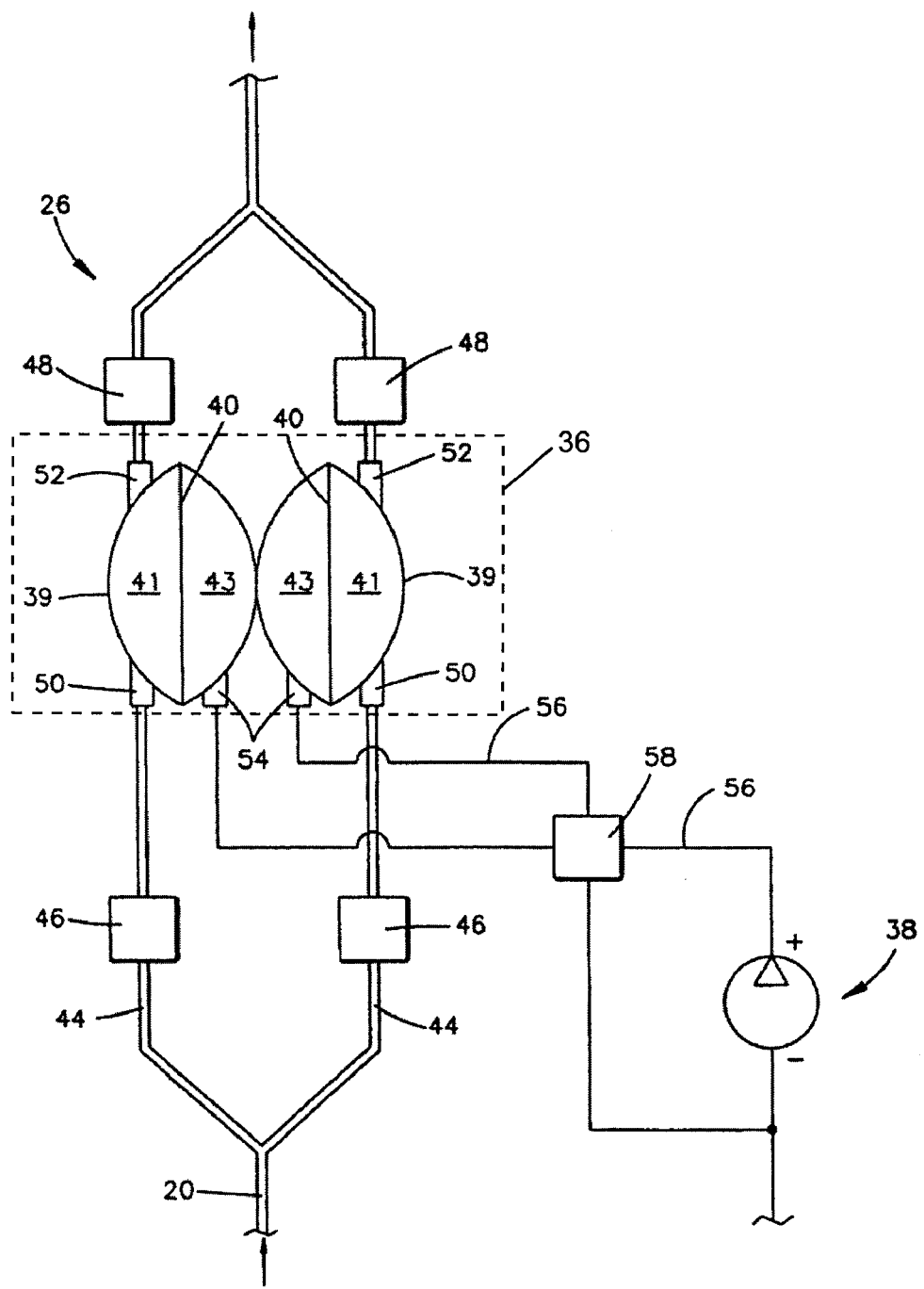
FIG. 1A is a schematic view of part of the system of FIG. 1.

The dialysis systems shown schematically in the drawings have parts that are examples of the elements recited in the apparatus claims, and can be operated in steps that are examples of the elements recited in the method claims. The illustrated systems thus include examples of how a person of ordinary skill in the art can make and use the claimed invention. They are described here to meet the enablement and best mode requirements of the patent statute without imposing limitations that are not recited in the claims.

The apparatus 10 shown in FIG. 1 is a renal dialysis system for the extracorporeal treatment of blood from a patient whose kidney function is impaired. The dialysis system comprises a blood circuit 12 through which the patient's blood travels, a dialyzer 13 that serves to separate the wastes from the blood, and a dialysate circuit 14 through which treatment fluid, specifically dialysate, travels carrying the waste away. The claims define an apparatus and method of recirculating blood through a blood treatment system such as the dialysis system shown in FIG. 1.

The dialysate circuit 14 includes a dialysate pump 15 for driving dialysate fluid around the dialysate circuit 14 and through the dialyzer 13. The dialysate circuit 14 may further include other components such as those described in U.S. patent application Ser. No. 11/148,928, entitled Dialysis System and filed on Jun. 9, 2005, which is hereby incorporated by reference.

The dialyzer 13 is a known device that contains a semi-permeable membrane 16 that separates a blood compartment 17 from a dialysate fluid compartment 18. The dialyzer 13 operates such that blood flows in one direction through the blood compartment 17 while dialysate fluid flows in the opposite direction through the dialysate compartment 18. In this way, urea and other small blood impurities pass through the membrane 16 from the blood side 17 to the dialysate side 18, but blood cells and other blood components which are too large to pass through the membrane 16 are retained in the blood.

The blood circuit 12 includes an arterial line 20 for withdrawing blood from a patient and delivering it to the dialyzer 13, and a venous line 24 for returning the treated blood to the patient. A blood pump 26 drives the blood around the circuit. The arterial line 20 incorporates a valve 30 that can stop the flow of blood from the patient, an air detector 32 that can detect air in the arterial line 20, and a flow sensor 34 that measures the flow of blood.

The blood pump 25 in the illustrated example is configured as described in U.S. patent application Ser. No. 10/399,128, entitled Device and Methods for Body Fluid Flow Control In Extracorporeal Fluid Treatments, filed Jul. 28, 2003, which is incorporated by reference. As shown schematically in FIG. 1A, the blood pump 26 thus includes a dual chamber device 36 and a source of pneumatic pressure 38. The dual chamber device 36 defines two chambers 39 that can be arranged in parallel, as shown in FIG. 1A, or in series, as shown in application Ser. No. 10/399,128. The two chambers 39 contain two flexible membranes 40. Each flexible membrane 40 divides a corresponding chamber 39 into first and second pumping chambers 41 and 43. A pair of arterial branch lines 44 with inlet and outlet valves 46 and 48 communicate the arterial line 20 with inlet and outlet ports 50 and 52 at the first pumping chambers 41. Gaseous ports 54 at the second pumping chambers 43 communicate with the source of pneumatic pressure 38 through pneumatic lines 56 and a directional valve 58.

The various parts of the blood pump 26 cooperate to pump blood through the venous line 20 in the direction indicated by the arrows shown in FIG. 1A. When the directional control valve 58 directs negative pneumatic pressure to either of the second pumping chambers 43, the adjacent flexible membrane 40 deflects to enlarge the first pumping chamber 41 and thereby to draw blood into the first pumping chamber 41. When the directional control valve 58 subsequently directs positive pneumatic pressure to the second pumping chamber 43, the flexible membrane 40 deflects back to constrict the first pumping chamber 41 and thereby to expel blood from the first pumping chamber 41. The inlet and outlet valves 46 and 48 are opened and closed accordingly. The dual chambers 39 are both operated in this manner to pump blood through the two branch lines 44.

The directional control valve 58 can provide the two gaseous ports 54 with positive pneumatic pressure at the same time, and with negative pneumatic pressure at the same time. The dual chambers 39 then move blood fully in phase with each other. If the directional control valve 58 provides the gaseous ports 54 with positive and negative pressures alternatively rather than simultaneously, the dual chambers 39 will move blood fully or partially out of phase with each other, depending on the degree to which the positive and negative pressures are out of phase with each other. Importantly, when the dual chambers 39 expel blood out of phase, each chamber 39 acts as a compliant chamber for the other by receiving a volume of blood corresponding to the degree to which the two chambers 39 are out of phase. This can be an advantage in use of the recirculation mode of the claimed invention, as described more fully below.

Other components of the blood circuit 12 include a source of fluid, such as a saline bag 60, which communicates with the arterial line 20 via a branch line 62 and a valve 64. Additionally, an anticoagulant solution such as a heparin supply 65 may communicate with the arterial line 20 through a branch line 67 and a pump 68. It is understood by persons skilled in the art that additional elements may be added to the blood circuit 12, such as air detectors in the branch lines 62 or 67. These additional elements are omitted from the drawings for clarity of illustration. Finally, the venous line 24 delivers the treated blood from the dialyzer 13 to the patient and also includes a valve 70, an air detector 72 and a flow sensor 74.

Figure 2:
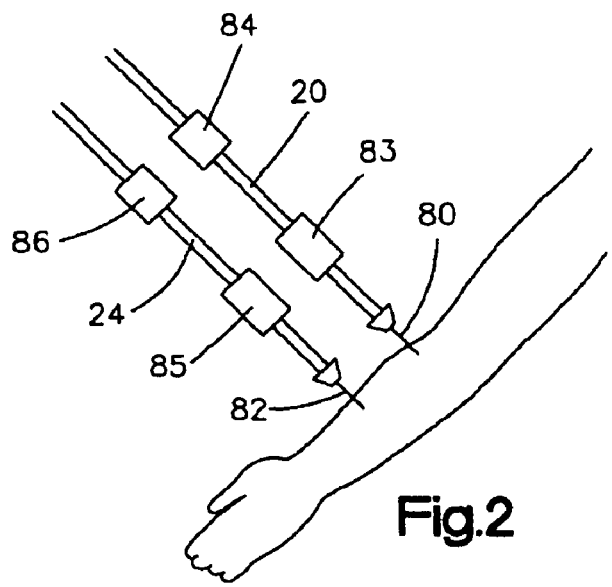
FIG. 2 is a schematic view of a patient connected to the arterial and venous lines of the system in FIG. 1.
Figure 3:
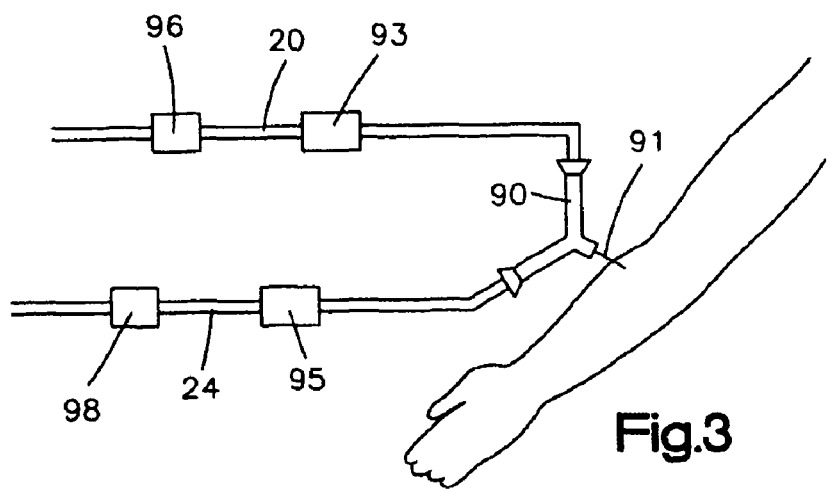
FIG. 3 is another schematic view of a patient connected to the arterial and venous lines of the system in FIG. 1.
Figure 4:
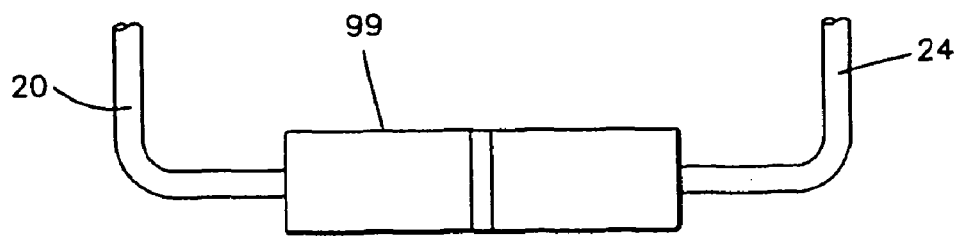
FIG. 4 is a schematic view of the arterial and venous lines of the system in FIG. 1 connected to each other.

The arterial and venous lines 20 and 24 can be coupled to the patient via separate patient connectors 80 and 82, as depicted in FIG. 2. The arterial line 20 also includes a manual clamp 83 and a connector 84. Similarly, the venous line 24 includes a manual clamp 85 and a connector 86. Alternatively, the arterial and venous lines 20 and 24 may be connected to the patient via a dual access connector 90 and a patient connector 91, which can be a needle or a catheter, as depicted in FIG. 3. Again, manual clamps 93, 95 and connectors 96, 98 are provided on the arterial and venous lines 20 and 24 respectively. In either case, the arterial and venous lines 20 and 24 can be disconnected from the patient by closing the manual clamps 83, 85 in the case of two connectors, or 93, 95 in the case of a dual access connector 90. The arterial and venous lines 20 and 24 may then be separated from the patient at the connectors 84, 86 or 96, 98 and connected together via an inter-connector 99, as depicted in FIG. 4.

A controller 100 coordinates the operation of the dialysis system 10 by controlling the blood flow in the blood circuit 12, the dialysate flow in the dialysate circuit 14, and the flow of saline or heparin to the arterial line 20 via the branch lines 62 and 67. To achieve this, the controller 100 utilizes hardware and/or software configured for operation of these components and may comprise any suitable programmable logic controller or other control device, or combination of control devices, that is programmed or otherwise configured to perform as recited in the claims. Thus, blood flow in the blood circuit 12 is controlled by operating the blood pump 26 and controlling the valves 30 and 70 in the arterial and venous lines 20 and 24. Dialysate flow in the dialysate circuit 14 is controlled by operating the dialysate pump 15.

The controller 100 is also responsive to various input signals it receives, such as input signals from one or more flow sensors 34 and 74 and air detectors 32 and 72. Additionally, the controller 100 displays system status and various other treatment parameters, known in the art, on a display screen that allows the operator to interact with the controller 100 via an operator interface. The operator interface of the display screen may be in the form of a series of buttons, a touch sensitive control screen, or any other means that allow an operator to interact with the controller 100.

Having detailed the various components of the dialysis system 10, now follows a description of how the various parts function to effect recirculation of blood within the blood circuit 12.

The controller 100 has at least two modes of operation. One is a standard dialysis treatment mode during which blood is withdrawn from the patient, pushed through the blood circuit 12 in the direction indicated by arrow 182, and delivered back to the patient while dialysate solution is circulated through the dialysate circuit 14 and dialyzer 13 in the direction indicated by arrow 184. During this mode, the valves 30 and 70 in the arterial and venous lines 20 and 24 are kept open to effect the withdrawal and delivery of blood to the patient. The driving force of the positive and negative pneumatic pressures at the blood pump 26 are determined by the controller 100 in response to the blood flow rates sensed by the flow sensors 34 and 74. During this standard dialysis treatment mode, saline or heparin may be delivered to the arterial line 20 via the corresponding branch lines 62 and 67. The dialysate pump 15 drives the dialysate solution around the dialysate circuit 14 and is activated by the controller 100 in response to a set of preprogrammed parameters and inputs such as the dialysate flow rate and other input signals known in the art that may take part in the performance of a dialysis treatment on a patient.

Figure 5B:
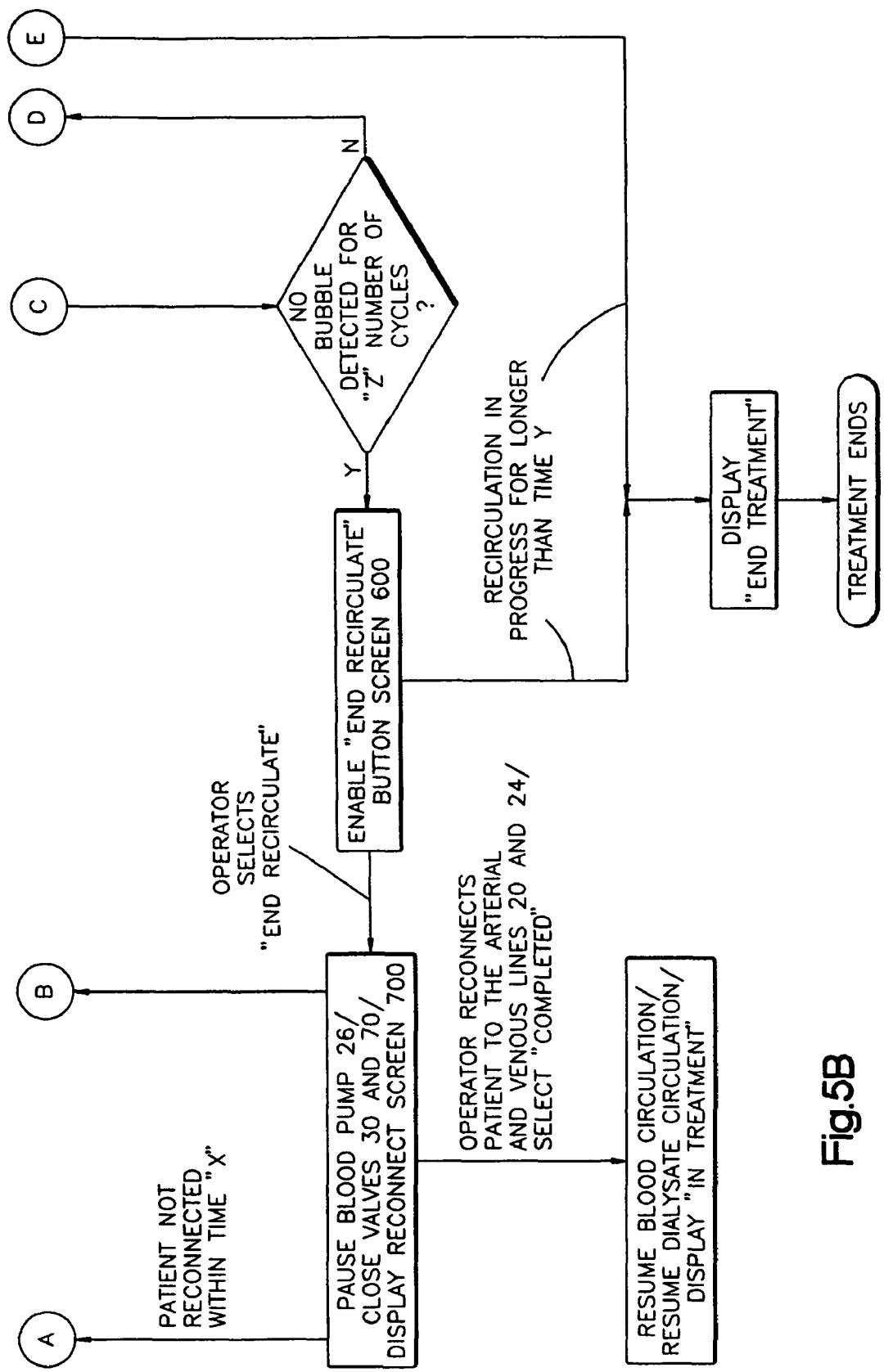
FIG. 5 is a flow chart representing the steps involved in recirculation of blood in the system of FIG. 1.

A second mode preprogrammed into the controller 100 is the recirculation function during which blood circulates in the blood circuit 12 in a closed loop bypassing the patient while dialysate fluid circulation is paused. The recirculation mode can be used in at least two instances; when a patient needs to temporarily disconnect from the dialysis system 10, or when air is detected in the blood circuit 12. In either case, an operator, who may be the patient, can interact with the controller 100 to initiate the recirculation mode. The steps for the recirculation mode are outlined in FIG. 5.

Figure 6:
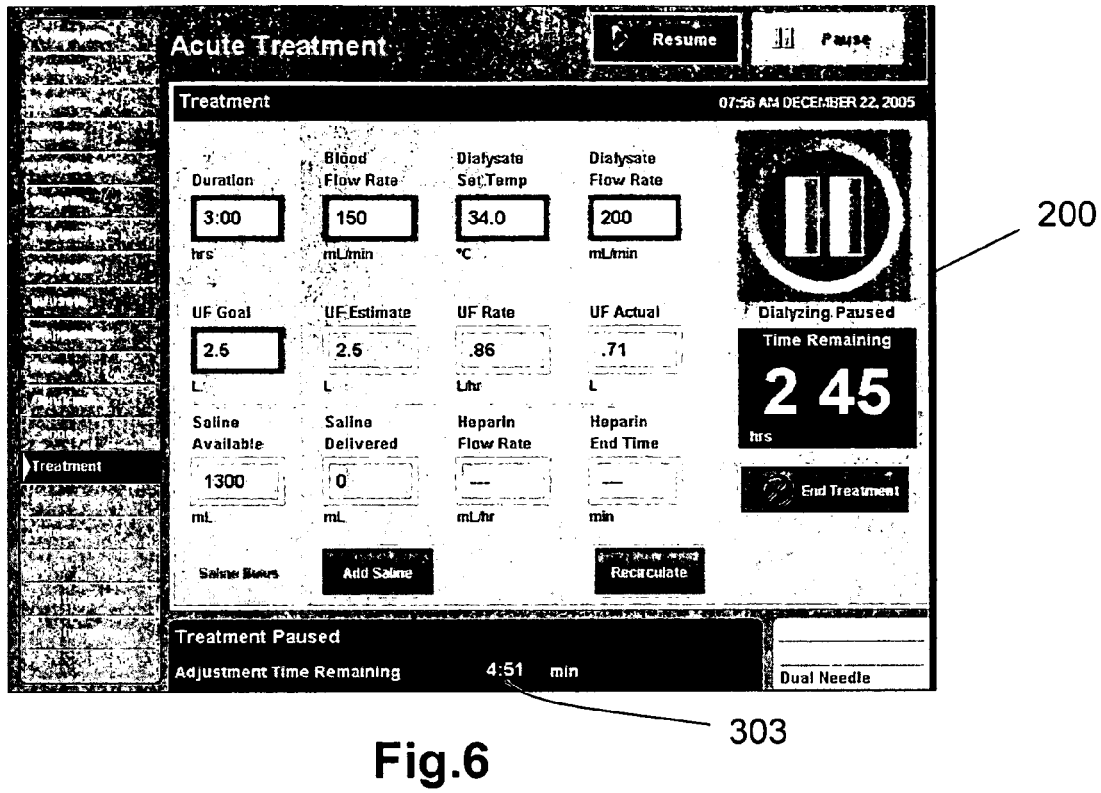
FIGS. 6-12 are examples of display screens and their user interface areas for the system in FIG. 1.
Figure 7:
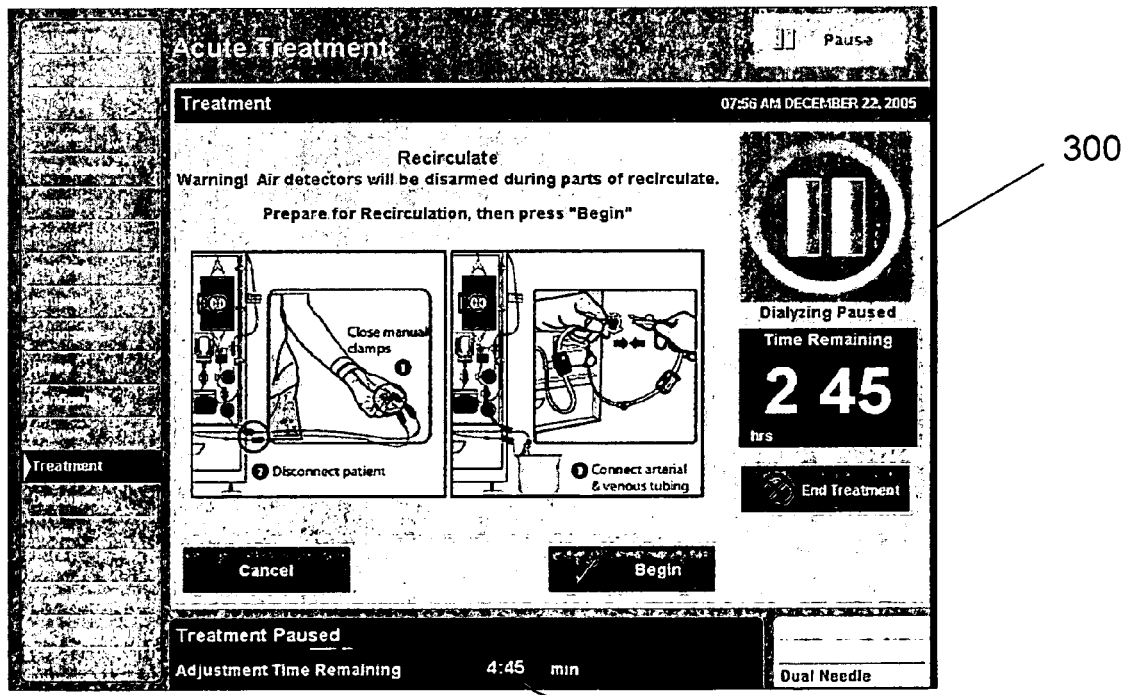
Figure 8:
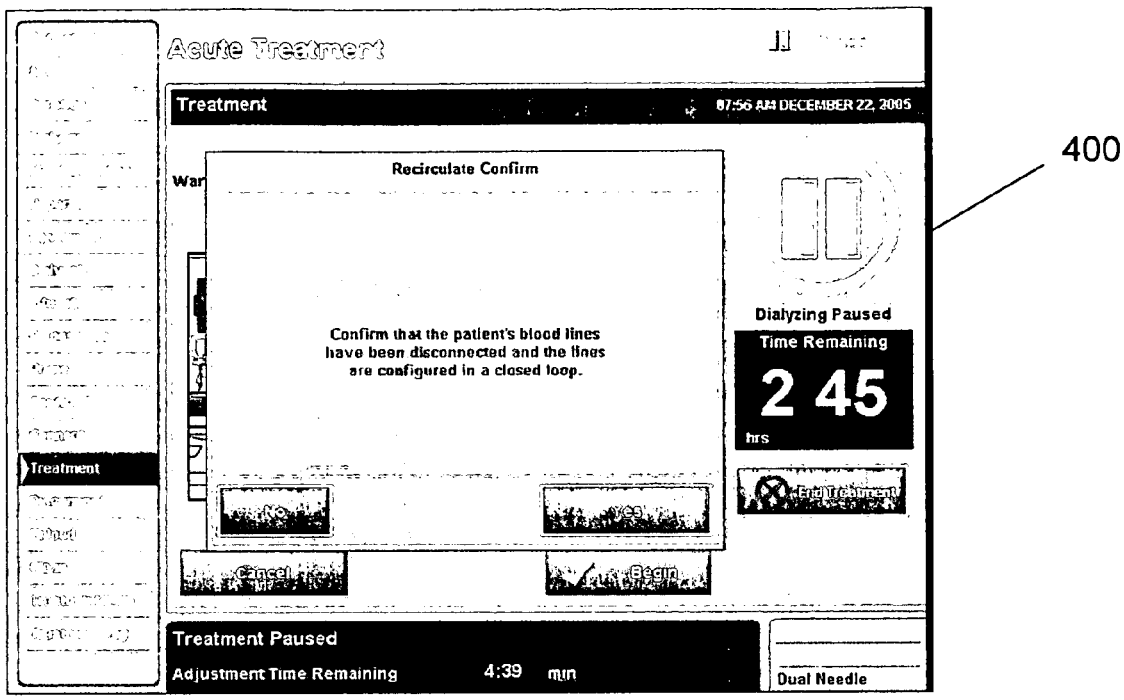

When a patient needs to temporarily disconnect from the dialysis system 10, the operator may pause treatment by interacting with the controller 100. This selection prompts the controller 100 to pause the blood pump 26, pause the dialysate pump 15, close the valves 30 and 70 adjacent to the patient, and display a "Treatment Paused" screen 200, such as the one depicted in FIG. 6. The operator then selects "Recirculate" on the operator interface of the controller 100, in this example the display screen 200. In response, the controller 100 displays a "Recirculation Setup" screen 300, such as the one depicted in FIG. 7. The operator is allowed a predetermined amount of time x to prepare for recirculation by disconnecting the arterial and venous lines 20 and 24 from the patient and connecting the two lines together. The recirculation setup screen 300 alerts the operator that treatment has been paused and displays a countdown clock 303 which indicates the length of time the operator has to prepare for recirculation. The setup screen 300 also provides instructions for the steps the operator must take to prepare for recirculation. These steps include (i) closing the manual clamps 83, 85 or 93, 95; (ii) separating the arterial and venous lines 20 and 24 from the patient at the connectors 84, 86 or 96, 98; and (iii) connecting the arterial and venous lines 20 and 24 together via the interconnector 99 to form a closed loop.

While the controller 100 displays the recirculation setup screen 300, the blood pump 26 can be stopped for a maximum time x. This avoids coagulation that might otherwise occur if the blood were permitted to remain stationary in the blood circuit 12 for a longer period. Time x is predetermined on the basis of clinical and practical considerations, and is preprogrammed into the controller 100. In this example, time x is five minutes. Time x, however, may have a different value as long as the value will ensure that the standing blood does coagulate. To ensure that the operator is aware of the passage of time x, the controller 100 will display a countdown clock, as described above, and will sound an alarm periodically such as every minute. If during time x the operator fails to cancel the recirculation selection or fails to disconnect the patient and start recirculation, the controller 100 sounds a different alarm and displays a screen alerting the operator that treatment must end.

Figure 9:
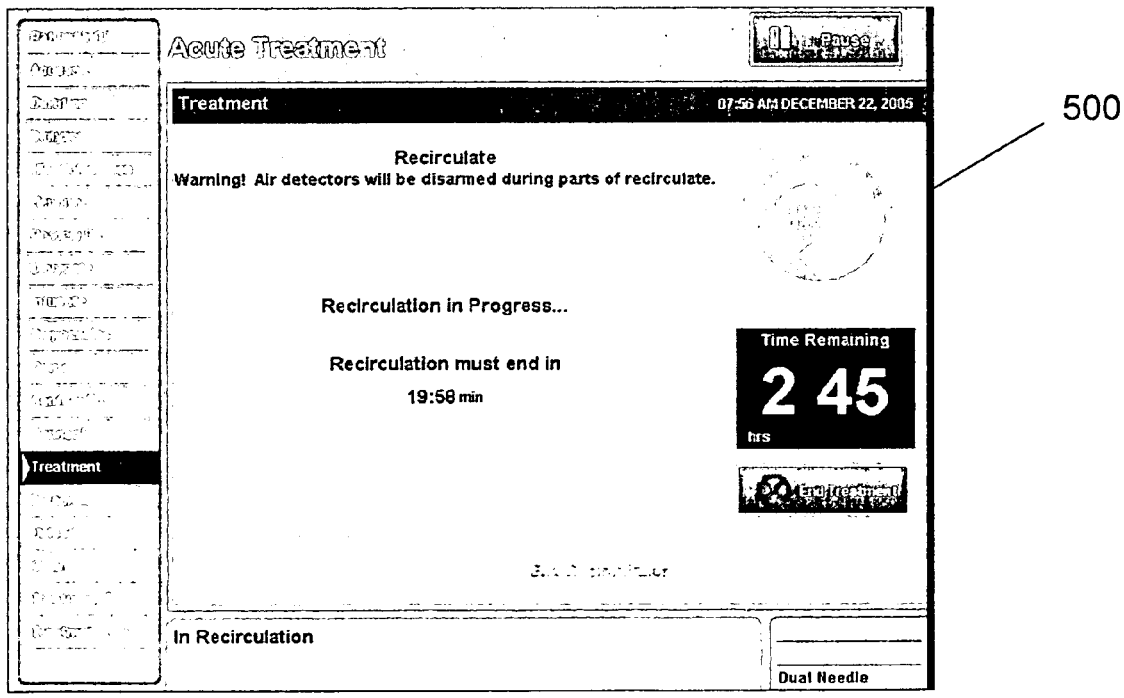

If the steps for disconnecting the patient have been performed successfully during the allowed time x, the operator can interact with the setup screen 300 to begin recirculation, e.g. by pressing the "Begin" button on the setup screen 300. At this prompt, the controller 100 displays a "Confirm Recirculation" screen 400. If the operator disconfirms by pressing "No", the controller 100 reverts back to displaying the recirculation setup screen 300. If the operator confirms preparation by pressing "Yes," the controller 100 starts recirculation of blood by reactivating the blood pump 26 and reopening the valves 30 and 70 adjacent to the patient while the dialysate pump 15 remains inactive. The controller 100 then resumes blood flow in the direction of the arrow 182. Preferably, the controller 100 operates the blood pump 26 with the two chambers 39 in phase during the standard dialysis treatment mode, and switches the blood pump 26 to a condition in which the two chambers 39 operate out of phase, and preferably fully or 180° out of phase, in the recirculation mode. Compared with in-phase operation of the dual chambers 39, the compliant chamber in out-of-phase operation provides volume needed for the blood to flow through the closed loop of the blood circuit 12 during recirculation. The controller 100 alerts the operator that recirculation is in progress by displaying a "Recirculation In Progress" screen 500, such as the one depicted in FIG. 9.

Recirculation may proceed for only a predetermined amount of time y. The screen 500 alerts the operator as to when recirculation must end by displaying a countdown clock. During the last few minutes of the countdown, an alarm will sound prompting the operator to reconnect to the dialysis system 10 and to run the system in the normal dialysis treatment mode. As with time x, the controller 100 is programmed with a predetermined time y. In this example, time y is 20 minutes and the alarm is set to sound periodically during the last five minutes. These times, however, may have different values as long as the values will ensure that the recirculating blood does not coagulate. If the operator fails to reconnect the patient and resume treatment at the end of time y, the controller 100 displays a screen alerting the operator that recirculation must end.

Figure 10:
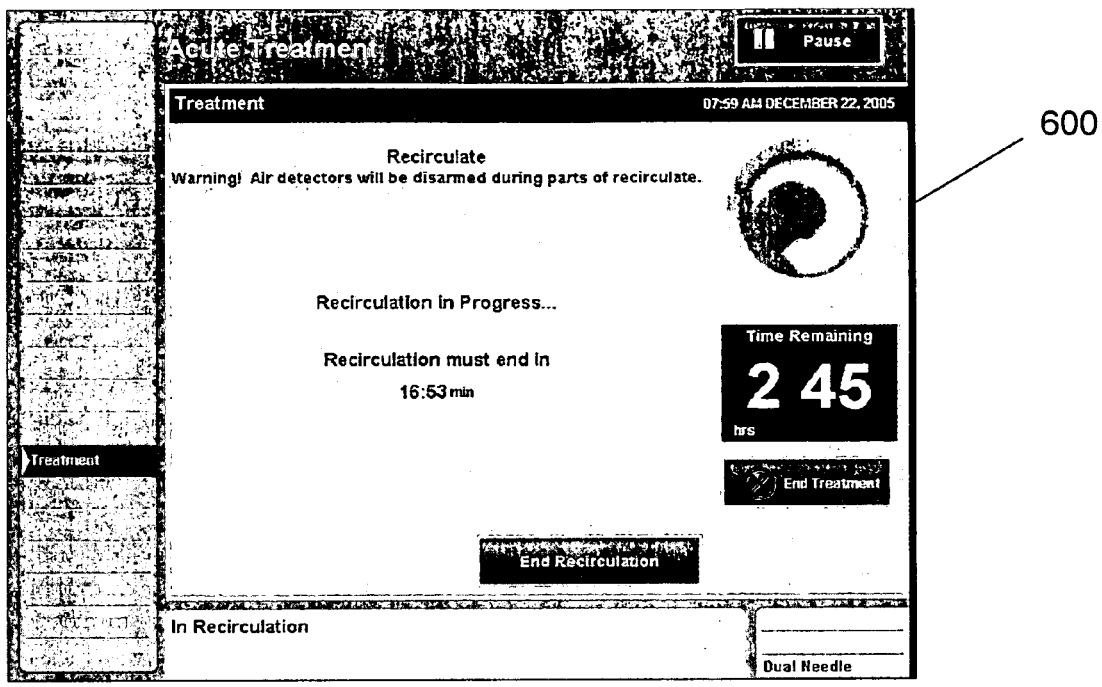

The operator is also not able to stop recirculation unless the controller 100 detects no air in the arterial and venous lines 20 and 24 for a number z of uninterrupted blood cycles. Thus, initially, on the display screen 500, the "End Recirculation" button is not enabled. Once the air detectors 32 and 72 do not detect air the number z of cycles, the controller 100 displays a screen 600, such that depicted in FIG. 10, where the "End Recirculation" button is enabled. The number z also has a predetermined valve in the controller 100 which, in this example, is 2 cycles.

Figure 11:

During the allowed time y and while screen 600 is displayed, the operator can interact with the operator interface to end recirculation by pressing the enabled "End Recirculation" button. At this command, the controller 100 stops the flow of blood by pausing the blood pump 26 and closing the valves 30 and 70. The controller 100 then displays a "Reconnect Patient Access" screen 700, such as the screen depicted in FIG. 11, which alerts the operator that recirculation has stopped, shows the predetermined time x during which the operator must reconnect the patient to the dialysis system 10, and displays instructions for reconnecting the patient. Once the patient has been reconnected to the dialysis system 10, the operator can interact with the operator interface, e.g. by pressing the "Completed" button on screen 700. The controller 100 then restarts blood flow through the blood circuit 12 by opening the valves 30 and 70 and restarting the blood pump 26, preferably with in-phase operation of the dual chambers 39. The controller 100 also restarts dialysate fluid flow through the dialysate circuit 14 by reactivating the dialysate pump 15. In this manner, normal treatment and molecular exchange between the blood and dialysate fluid is resumed in the dialyzer 13. Operation of the saline valve 64, which is preferably maintained in a closed condition throughout the recirculation mode to block blood from entering the saline reservoir 60, can likewise be resumed as needed during the treatment mode.

Figure 12:
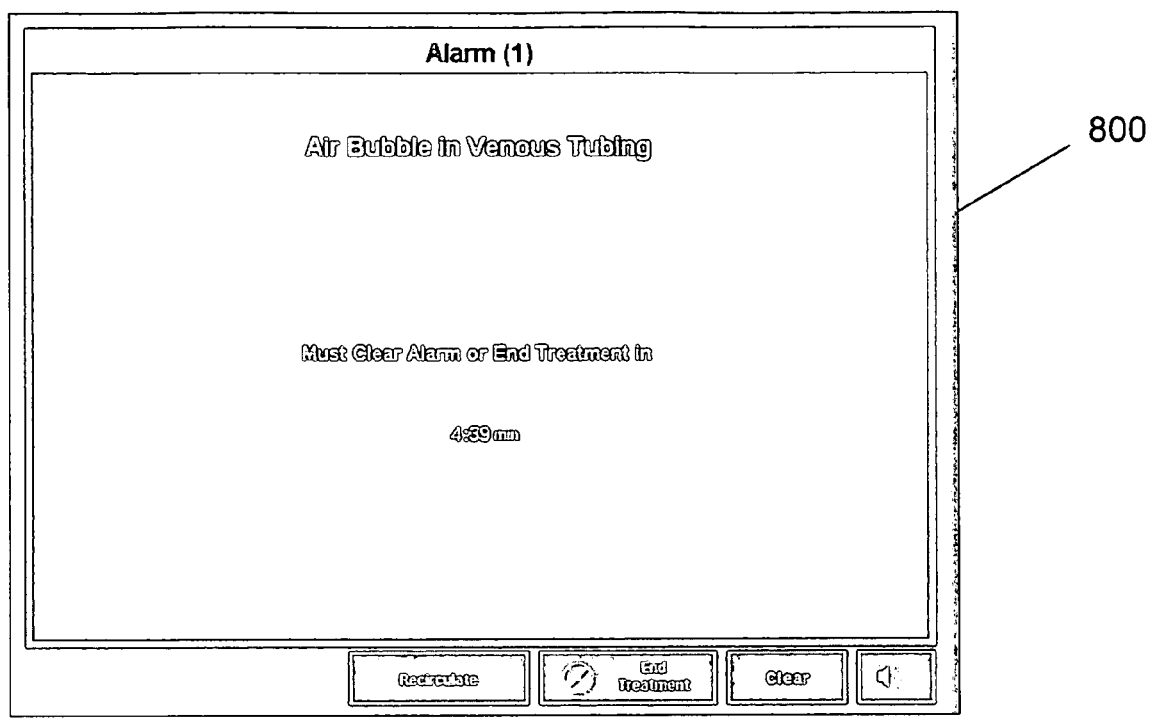

The controller 100 can also prompt an operator to start the process of recirculating blood when air is detected by the air detectors 32 or 72. When air is detected in the blood circuit 12, the controller pauses the blood pump 26 and the dialysate pump 15, sounds an alarm and displays an "Air Detected" screen 800, such as the one shown in FIG. 12. This screen alerts the operator that air has been detected and displays a "Recirculate" button that allows the operator to initiate blood recirculation. When the operator selects "Recirculate," the controller 100 will display the "Recirculation Setup" screen 300 and the operator and controller 100 can interact, following the same steps as described previously, to effect recirculation of blood. As mentioned above, the operator is not able to stop recirculation unless the blood has completed a predetermined number z of uninterrupted cycles around the blood circuit 12 without the detectors detecting air. This ensures that the blood circuit 12 has been purged of air before dialysis can be resumed. Recirculating blood through the blood circuit 12, and though the dialyzer 13, removes air from the blood as the air becomes trapped in the top portion of the dialyzer 13. However, it may be preferable to drive air upward into the saline bag 60. The controller 100 can accomplish this by holding the saline valve 62 open, and by operating the blood pump 26 with the dual chambers 39 in phase with each other (and preferably fully in phase with each other) so that the closed blood recirculation circuit 12 does not obtain the volume of a compliant chamber 39. In the absence of a compliant chamber 39 at the blood pump 26, the saline bag 60 will provide the volume needed to capture air from the closed circuit 12.

As previously, if the blood pump 26 is paused for longer than the allowed time x, e.g. because the operator failed to initiate recirculation while the "Air Detected" screen 800 is displayed, the controller 100 will again sound an alarm and alert the operator that treatment must end. To ensure that the operator is aware of this time limitation, the "Air Detected" screen 800 displays a count down clock and clearly states that the operator must either clear the alarm (by initiating recirculation) or end treatment by the end of the counted down time.

This written description sets forth the best mode of the invention, and describes the invention so as to enable a person skilled in the art to make and use the invention, by presenting examples of the elements recited in the claims. The patentable scope of the invention is defined by the claims, and may include other examples that occur to those skilled in the art. Such other examples, which may be available either before or after the application filing date, are intended to be within the scope of the claims if they have elements that do not differ from the literal language of the claims, or if they have equivalent elements with insubstantial differences from the literal language of the claims.

What is claimed is:

1. An extracorporeal blood treatment apparatus comprising:
    a blood treatment unit;
    a treatment fluid circuit including a treatment fluid pump operative to circulate treatment fluid around the treatment fluid circuit and through the blood treatment unit;
    a blood circuit including a blood pump operative to circulate blood around the blood circuit and through the blood treatment unit, an arterial line for withdrawing blood from a patient, and a venous line for returning the treated blood to the patient, the blood pump comprising two chambers and the arterial and venous lines being configured to be switched between a first condition in which they are connected to the patient and a second condition in which they are disconnected from the patient and connected to each other for recirculation of blood through the blood circuit; and
    a controller configured to operate the pumps in a treatment mode during which both the blood pump and the treatment fluid pump are operated to circulate blood and treatment fluid through the blood treatment unit while the arterial and venous lines are in the first condition, and in a recirculation mode during which the treatment fluid pump is inactivated and the blood pump is operated to circulate the blood through the blood circuit while the arterial and venous lines are in the second condition.

2. The apparatus of claim 1 wherein the controller is configured to switch the blood pump between a condition in which the dual chambers operate in phase with each other and a condition in which the dual chambers operate out of phase with each other.

3. The apparatus of claim 2 wherein the controller is further configured to operate the blood pump such that the dual chambers are out of phase during the recirculation mode.

4. The apparatus of claim 1 further comprising an input device coupled to the controller and operative to allow an operator to input a command to the controller to initiate the recirculation mode.

5. The apparatus of claim 1 further comprising an input device coupled to the controller and operative to allow an operator to end the recirculation mode.

6. The apparatus of claim 1 further comprising a bubble detector and an input device coupled to the controller and operative to alert an operator when the bubble detector detects a bubble in the blood circuit and operative to allow the operator to input a command to the controller to initiate the recirculation mode.

7. The apparatus of claim 1 further comprising a bubble detector and wherein the controller is further configured to continue the recirculation mode until the bubble detector does not detect a bubble in the blood circuit for a predetermined number of cycles of recirculation.

8. The apparatus of claim 1 wherein the controller is configured to display instructions for switching the arterial and venous lines from their first condition to their second condition after the recirculation mode is initiated.

9. The apparatus of claim 1 wherein the controller is configured to pause the blood pump when recirculation is initiated to allow time for switching the arterial and venous lines from their first condition to their second condition.

10. The apparatus of claim 8 wherein the controller is further configured to prompt the operator to end treatment when the blood pump has been paused for a predetermined amount of time x.

11. The apparatus of claim 9 wherein the controller is configured to display a countdown time remaining to the end of time x.

12. The apparatus of claim 9 wherein the controller is configured to sound an alarm before the end of time x.

13. The apparatus of claim 1 wherein the controller is configured to prompt the operator to end treatment when the recirculation mode has been operating for a predetermined amount of time y.

14. The apparatus of claim 13 wherein the controller is configured to display a countdown time remaining to the end of time y.

15. The apparatus of claim 13 wherein the controller is configured to sound an alarm before the end of time y.

16. The apparatus of claim 1 wherein the blood treatment unit is a dialyzer.

* * * * *